United States Patent
Sellers et al.

(10) Patent No.: US 10,010,386 B2
(45) Date of Patent: Jul. 3, 2018

(54) DENTAL BLANK HOLDER

(71) Applicant: Ivoclar Vivadent AG, Schaan (LI)

(72) Inventors: James M. Sellers, Eliot, ME (US); Douglas B. Snell, Portsmouth, NH (US); Michael R. Cole, Stratham, NH (US); James Donnelly, Ipswich, MA (US)

(73) Assignee: Ivoclar Vivadent AG, Schaan (LI)

( * ) Notice: Subject to any disclaimer, the term of this patent is extended or adjusted under 35 U.S.C. 154(b) by 45 days.

(21) Appl. No.: 14/667,659

(22) Filed: Mar. 24, 2015

(65) Prior Publication Data

US 2016/0278891 A1   Sep. 29, 2016

(51) Int. Cl.
| | | |
|---|---|---|
| *B23C 3/35* | (2006.01) | |
| *A61C 13/00* | (2006.01) | |
| *B23C 3/00* | (2006.01) | |
| *B23Q 3/06* | (2006.01) | |

(52) U.S. Cl.
CPC ............ *A61C 13/0022* (2013.01); *B23C 3/00* (2013.01); *B23Q 3/061* (2013.01); *B23C 2226/18* (2013.01); *Y10T 409/30868* (2015.01)

(58) Field of Classification Search
CPC ..... B23C 2226/18; A61C 13/00; A61C 13/08; A61C 13/083; A61C 13/0004; A61C 13/0009; B23Q 3/061; Y10T 409/30868
USPC ..... 269/40, 43, 45, 160, 233, 237–239, 275, 269/229
See application file for complete search history.

(56) References Cited

U.S. PATENT DOCUMENTS

| | | | | |
|---|---|---|---|---|
| 2,354,919 | A * | 8/1944 | Lockwood | F16L 3/2235 248/68.1 |
| 2,684,700 | A * | 7/1954 | Bain | B25B 5/106 269/160 |
| 5,201,502 | A * | 4/1993 | Schneider | B25B 5/10 269/221 |
| 6,224,371 | B1 | 5/2001 | De Luca | |
| 6,482,284 | B1 | 11/2002 | Reidt et al. | |
| 6,485,305 | B1 | 11/2002 | Pfeiffer | |
| 6,627,327 | B2 | 9/2003 | Reidt et al. | |
| 6,660,400 | B1 | 12/2003 | Hintersehr | |
| 6,669,875 | B2 | 12/2003 | Meyertholen et al. | |
| 6,769,912 | B2 | 8/2004 | Beuschel et al. | |
| 6,775,581 | B2 | 8/2004 | Landers et al. | |
| 6,979,496 | B2 | 12/2005 | Haymann et al. | |
| 6,991,853 | B2 | 1/2006 | De Luca et al. | |

(Continued)

FOREIGN PATENT DOCUMENTS

WO   20131175440   8/2013

*Primary Examiner* — Daniel Howell
(74) *Attorney, Agent, or Firm* — Hodgson Russ LLP (57) ABSTRACT

A dental blank holder for the manufacture of dental articles. The dental blank holder can include a frame configured to cooperate with a blank holder of a dental mill. The frame can includes an inner periphery and an outer periphery, the inner periphery including a plurality of receiving walls forming receiving spaces, each receiving space configured to receive a dental blank. The dental blank holder may also include a movable arm configured to form a plurality of locking walls, each locking wall configured to enclose a corresponding receiving space, the movable arm including at least one biasing member configured to apply an individual force toward each receiving space such that each of the dental blanks is held in the receiving spaces for a milling process.

19 Claims, 12 Drawing Sheets

(56) References Cited

U.S. PATENT DOCUMENTS

| | | | |
|---|---|---|---|
| 7,024,272 B2 | 4/2006 | Thomas et al. | |
| 7,110,849 B2 | 9/2006 | Landers et al. | |
| 7,214,435 B2 | 5/2007 | Meyertholen et al. | |
| 7,234,938 B2 | 6/2007 | Bodenmiller | |
| 7,556,460 B2 | 7/2009 | Steger | |
| 8,568,897 B2* | 10/2013 | Ganley | A61C 13/0022 409/163 |
| 8,622,377 B2* | 1/2014 | Konrad | A61C 13/0022 269/287 |
| 8,820,726 B2* | 9/2014 | Yeom | B23Q 1/5406 269/249 |
| 9,265,592 B2* | 2/2016 | Koch | A61C 13/0003 |
| 9,421,653 B2* | 8/2016 | Suyama | B23C 3/16 |
| 2006/0106485 A1 | 5/2006 | Landers et al. | |
| 2006/0115794 A1 | 6/2006 | Sager | |
| 2007/0136031 A1 | 6/2007 | Feldman et al. | |
| 2007/0241490 A1* | 10/2007 | Myers | B25B 1/103 269/43 |
| 2009/0274994 A1* | 11/2009 | Jung | A61C 13/0022 433/202.1 |
| 2009/0275000 A1 | 11/2009 | Jung | |
| 2012/0214133 A1* | 8/2012 | Jung | A61C 8/005 433/174 |
| 2014/0023873 A1 | 1/2014 | Ganley | |
| 2016/0158903 A1* | 6/2016 | Konrad | B23Q 3/103 269/309 |
| 2016/0193020 A1* | 7/2016 | Fix | A61C 8/005 29/896.1 |

\* cited by examiner

DENTAL BLANK HOLDER

FIELD OF THE DISCLOSURE

The disclosure generally relates to the field of dental prosthesis and restorations.

BACKGROUND OF THE DISCLOSURE

There is a progressively increasing trend in dentistry toward the use of automated technologies for treatment planning, virtual procedures, orthodontics, design and manufacturing of dental restorations both in dental offices (chair side) and dental laboratories (lab side). This trend, sometimes called the "digital revolution," is most evident in the explosion of CAD/CAM technologies on the lab side. A number of CAD/CAM systems that are available to dental laboratories has increased nearly ten-fold in the last decade. Currently, there are over 25 dental CAD/CAM systems and quite a few copy-milling systems using mill blanks in a variety of shapes and sizes. Blank shapes vary from simple geometries such as rectangular, cylindrical or hexagonal to more complex such as smart blanks described in U.S. Pat. No. 6,979,496. Their sizes range from about 0.5" to about 4" in length or diameter. Mill blanks are available in all 4 types of materials—metals, polymers (resins, plastics), ceramics and composites. Ceramic mill blanks can be divided into three major categories: feldspathic (leucite-based and sanidine or feldspar-based), glass-ceramic (lithium silicate, micaceous, etc.), and crystalline ceramic based such as alumina and/or zirconia (soft-sintered or fully dense). All three ceramic categories as well as composite blanks are already available or soon will be available in a variety of shades. Stocking the necessary inventory of shades for each given type of blank adds to economic pressures on the facility operating a CAD/CAM system.

While CAD/CAM technology provides dental laboratories with opportunities for improved quality, reproducibility and elimination of human error, most CAD/CAM systems are geared to milling soft-sintered zirconia and thus lack material selection to be competitive in a supersaturated and fast-paced market. Since the price for a CAD/CAM system, depending on manufacturer and configuration, runs from $50,000 to $500,000 only the large labs and milling centers can afford to operate multiple systems to expand their material selection. Most CAD/CAM systems manufacturers do not make their own blocks, rather they purchase them from suppliers such as Ivoclar, with an established core competency in dental or advanced materials development and manufacturing. Understandably, CAD/CAM materials are fairly expensive adding substantially to CAD/CAM system operating costs. For example, the price of ceramic milling blanks range from about $0.60 to $4.50 per gram of material. Yield per blank as defined in U.S. Pat. No. 6,979, 496 is fairly low and most of it goes to waste.

The first CAD/CAM systems comprising milling units for chair side or lab side use such as Cerec (Sirona) and Lava (3M/ESPE) were closed systems wherein mill blanks are attached to a stub retainer, projection, mandrel, holder or carrier body, which have a unique patented geometry as described in U.S. Pat. Nos. 6,485,305 and 6,769,912 and can also be protected by a bar-code, thereby preventing interchangeability with other (CAD/CAM) systems. Variations of a work piece (millable part) on a stub assembly are also described in U.S. Pat. Nos. 7,214,435, 6,669,875, 6,627,327, 6,482,284, 6,224,371, 6,991,853 and 6,660,400. With the advent of open architecture systems, blank interchangeability between systems has become not only possible but extremely desirable. While the market is currently dominated by closed systems, the market penetration of open systems is steadily increasing. From 25 commercial CAD/CAM systems, at least 5 or 6 utilize the same D-250 dental 3D scanner and DENTALDESIGNER™ dental CAD software (3Shape A/S, Copenhagen, Denmark). In an open architecture system, the blanks are not bar-code protected and any blank can be used in these system.

Not all types of blanks can be economically produced in any shape and size. For example, zirconia and alumina blocks can be formed in any given shape and size to meet the demand for larger cases that can be milled from larger blanks. On the other hand, large feldspathic and glass-ceramic blanks are not so desirable due to a number of mechanical and economic constraints.

U.S. Patent Application 2006/0115794 appears to teach a system for continuous production of prosthodontic pieces such as crown cores, crowns or the like. The system utilizes turning and milling on a live central computer numerical control CNC machine of a zirconia rod stock that is automatically fed into the machine. Multiple pieces are cut one after another from the continuous rod stock. This patent application further appears to teach utilization of multiple machines wherein each machine is fed a rod stock of a different shape and/or size. A central control unit obtains specifications for a piece that is to be cut and selects the machine on which the piece is to be made by determining the rod stock that will require the least amount of cutting. In addition to the above mentioned economical and processing difficulties of fabricating and milling long rod stock from materials other than fully dense zirconia, considering the cost of the CNC machine, it is far more advantageous to enable one machine to mill all cases than to have many machines, each dedicated to a certain type of case.

U.S. Pat. No. 7,234,938 appears to disclose the multi-blank holder or workpiece receiver constructed as an elongated strip with multiples bores in it for embedding a plurality of identical blanks or workpieces. The invention relates to a milling/grinding machine, wherein, the workpiece receiver or mill blank holder has a plurality of bores arranged along its longitudinal axis, for receiving the workpieces or blanks. This invention also comprises a moldable embedding material disposed within the through-bore for retaining the workpiece within the through-bore. It further teaches a milling/grinding machine, comprising an embedding device for the automatic embedding of the workpiece in the workpiece receiver.

U.S. Patent Application 2006/0106485 describes the use of a virtual blank corresponding to a physical blank being processed to form a plurality of manufacturing features. This application further teaches virtual machining of each manufacturing feature of the plurality of manufacturing features into the virtual blank wherein each manufacturing feature exhibits an associative relationship with the coordinate system. Manufacturing instructions are generated to create the actual part by machining the plurality of manufacturing features into the blank. Such methods were pioneered in the automotive industry and described in U.S. Pat. Nos. 6,775, 581; 7,024,272; 7,110,849 and U.S. Patent Application 2006/0106485. It is also described in the white paper: Horizontal Modeling & Digital Process Design. The approach of electronically designing an article comprising an assembly of components is described in US Application 2007/0136031. Again, this disclosure is not related to dentistry.

Thus, a need exists in the art for enabling blank interchangeability, maximizing yield per blank, and reducing material waste, to maximize the system's versatility, selection of materials and efficiency of operation. There is also a desire to reduce inventory of blanks thus reducing operating costs associated with commercial CAD/CAM systems.

BRIEF SUMMARY OF THE DISCLOSURE

The present disclosure can be embodied as a dental blank holder for the manufacture of dental articles. The dental blank holder can include a frame configured to cooperate with a blank holder of a dental mill. The frame can include an inner periphery and an outer periphery, the inner periphery including a plurality of receiving walls forming receiving spaces, each receiving space configured to receive a dental blank. The dental blank holder may also include a movable arm configured to form a plurality of locking walls, each locking wall configured to enclose a corresponding receiving space, the movable arm including at least one biasing member configured to apply an individual force toward each receiving space such that each of the dental blanks is held in the receiving spaces for a milling process.

The present disclosure can also be embodied as a dental blank holder system for the manufacture of dental articles. The dental blank holder system can include a dental mill, a plurality of dental blanks, and a frame. The frame can be configured to cooperate with the dental mill, the frame including an inner periphery and an outer periphery. The inner periphery can include a plurality of receiving walls forming receiving spaces, each receiving space configured to receive a respective dental blank of the plurality of dental blanks. A movable arm can be configured to form a plurality of locking walls, each locking wall configured to enclose a corresponding receiving space. The movable arm may have at least one biasing member configured to apply an individual force toward each receiving space such that each of the dental blanks is held in the receiving spaces for a milling process.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

According to one aspect of the present disclosure, various dental blanks can be formed from individual blanks using prefabricated or custom-made frameworks to enable the use of individual blanks in the maximum possible number of systems. A dental blank can comprise dental blank of identical size and shade, or different shades, sizes and/or types of s dental blank. For example, a dental blank can comprise various sizes and shades of the same dental blank type and also a variety of different types of dental blanks from one or different manufacturers can be assembled on the same framework to make a "hybrid" dental blank. For example, E.MAX® CAD MO and/or LT blanks (Ivoclar) also known as "blue blocks" can potentially be processed by any robust CAD/CAM system utilizing wet-milling process and having software capable of designing full-contour restorations. An example of such a system capable of, but not yet milling "blue blocks" are ZENO® Tec system (Wieland), specifically ZENO® 4820 and ZENO® 3020 milling units interfaced with DENTALDESIGNER™ Software from 3Shape mentioned above.

Dental blanks may be arranged in an addressable matrix, whereby the addressable matrix is designed from parameters received from a history of prior milling operations or prior business operations. The dental blanks can have properties associated with parameters received from a history of prior milling operations or prior business operations. These properties can include type of material, material characteristics, size of the dental blank, shape of the dental blank, and/or shade of the dental blank. The parameters received from a history of prior milling operations can include type of case, material selection parameters, size of the dental article, shape of the dental article, shade of the dental article, optimal tool path, milling parameters, and statistics of milling envelopes used in the fabrication of dental articles. Examples of statistics of milling envelopes include shape and dimensions of the milling envelopes and the correlation of the milling envelopes with specific types of dental articles. Examples of milling parameters include type of tooling, depth of cut, feed rate, rotations per minute (rpm) and/or linear speed. Examples of type of tooling include a cutting, grinding or abrasive surface. The tooling can vary by material, shape, and/or size of tooling. Examples of cutting, grinding or abrasive surface include diamond, carbides, hardened steel, or ceramic. Examples of tooling shape include, but are not limited to cylindrical, conical, disc-shaped, ball-shaped, or fluted. The size of the tool may be dependent on diameter and length. Diamond tooling may include diamond grit. The depth of cut of the tooling may range in size from microns to millimeters. Further examples of milling parameters include post-milling parameters such as coating, glazing, or heat treatment parameters. Examples of parameters related to history of prior business operations include inventory used, inventory remaining, and case histories.

The dental blank holder 10 can be used for the manufacture of dental articles and include a frame 18 configured to cooperate with a blank holder of a dental mill (not shown). The frame 18 can include an inner periphery 18a and an outer periphery 18b, the inner periphery 18a can include a plurality of receiving walls 20 forming receiving spaces 22. Each receiving space 22 may be configured to receive a dental blank 12.

The blank holder 10 can include a movable arm 30 configured to form a plurality of locking walls 30a. Each locking wall 30a may be configured to enclose a corresponding receiving space 22. The movable arm 30 can include at least one biasing member 50 configured to apply an individual force toward each receiving space 22 such that each of the dental blanks 12 is held in the receiving spaces 22 for a milling process.

Figure 1A:
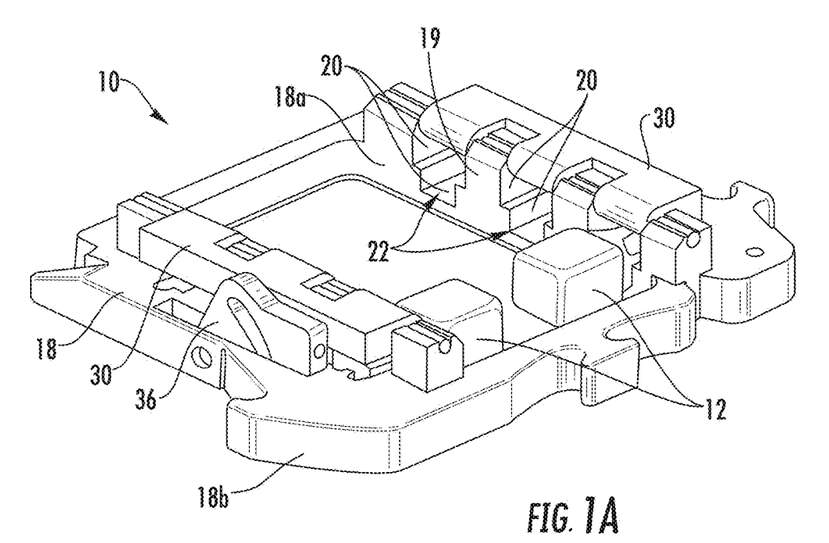
FIG. 1A is a perspective view of a device in a closed position according to an embodiment of the present disclosure.

The movable arm 30 can move between an open position (FIG. 1B) and a closed position (FIG. 1A). In an open position of the dental blank holder 10, dental blanks 12 may be moved into and out of the receiving spaces 22. In a closed position of the dental blank holder 10, the dental blanks 12 may be secured relative to the dental blank holder 10 for a milling operation. In one example, the movable arm 30 can be disposed across the receiving spaces 22 in order to form a locking wall 32 that is adjacent to the plurality of receiving walls 20. Consequently, each locking wall 32 that is formed by the arm 30 encloses a respective receiving space 22. However, as explained in detail below, each locking wall 32 may merely outline the receiving spaces 22 and not necessarily touch the dental blanks 12 received in the receiving spaces 22 in both the open and closed positions of the dental blank holder 10. Each of the dental blanks 12 are attached to frame 18. The frame 18 can be formed from a material suitable for holding the dental blanks 12 during a milling operation by a dental mill. For example, the frame 18 can be constructed from a metal or metal alloy such as steel or an aluminum alloy. In one particular example, the frame 18 is made of an austensic chromium-nickel stainless steel, such as Type 301 Stainless Steel made by AK Steel Corporation of West Chester, Ohio.

Figure 1B:
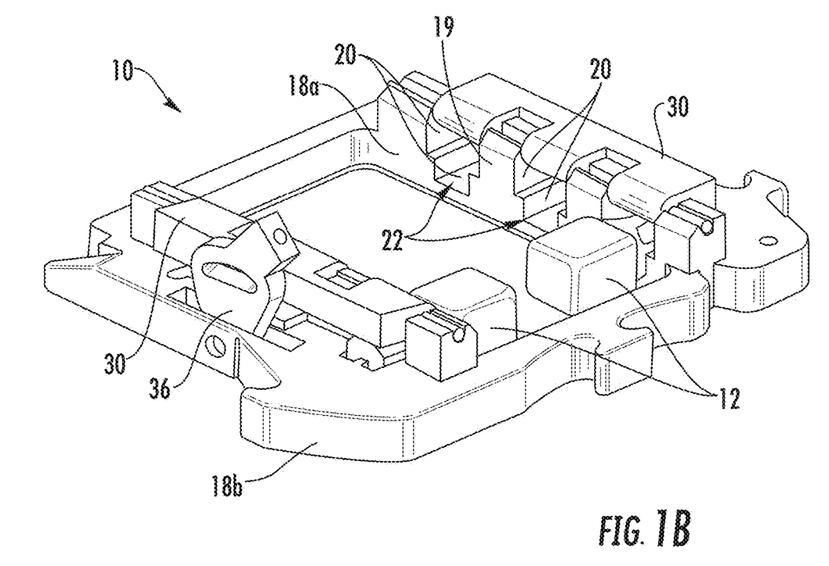
FIG. 1B is a perspective view of the device of FIG. 1A in an open position.
Figure 2:
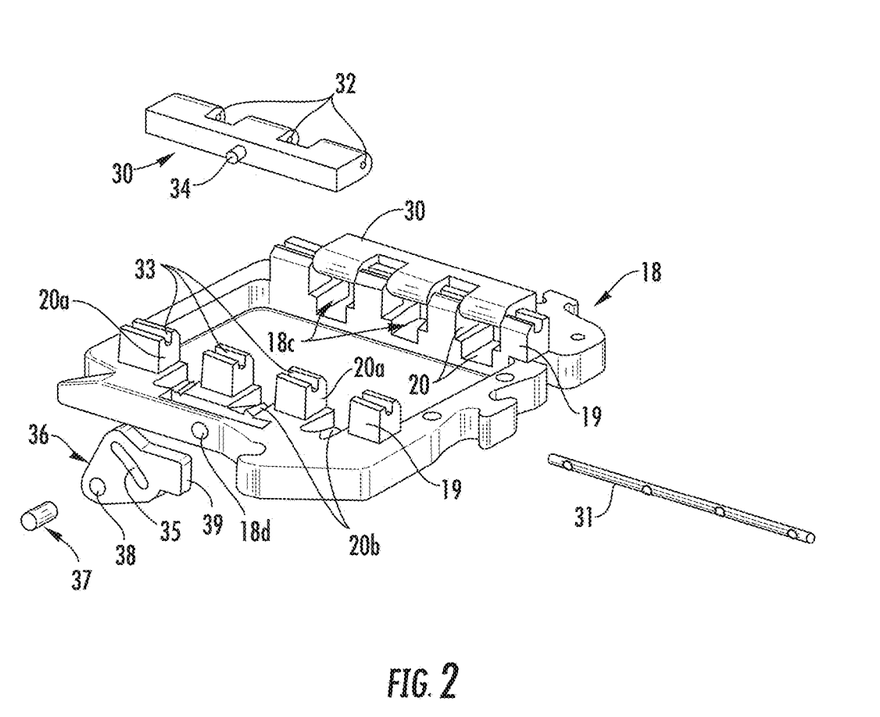
FIG. 2 is an exploded view of the device of FIGS. 1A and 1B.

FIG. 2 shows an exploded view of FIGS. 1A-1B, where one movable arm 30 is removed from the frame 18. As shown in FIG. 2, the movable arm 30 can be pivotable about a pivot shaft 31. The pivot shaft 31 can be received in apertures 32 of the movable arm 30 and in receiving slots 33 located on pillars 19 of frame 18. The lateral portions 20a of the receiving walls 20 may be defined by pillars 19, and lower portion portions 20b of the receiving walls 20 may be defined by recesses 18c in the frame 18. The pivot shaft 31 may be interweaved between the movable arm 30 and frame 18. The movable arm 30 can include a protrusion 34 that cooperates with a slot 35 in cam 36. The cam 36 may be rotatable relative about a pin 37, which may be received in an aperture 38 of cam 36 and a recess 18d of the outer periphery 18b of frame 18. The cam 36 may cooperate with an arm or other lever (not shown in FIG. 2) that can be attached, for example, in recess 39 of cam 36.

Figures 3A, 3B:
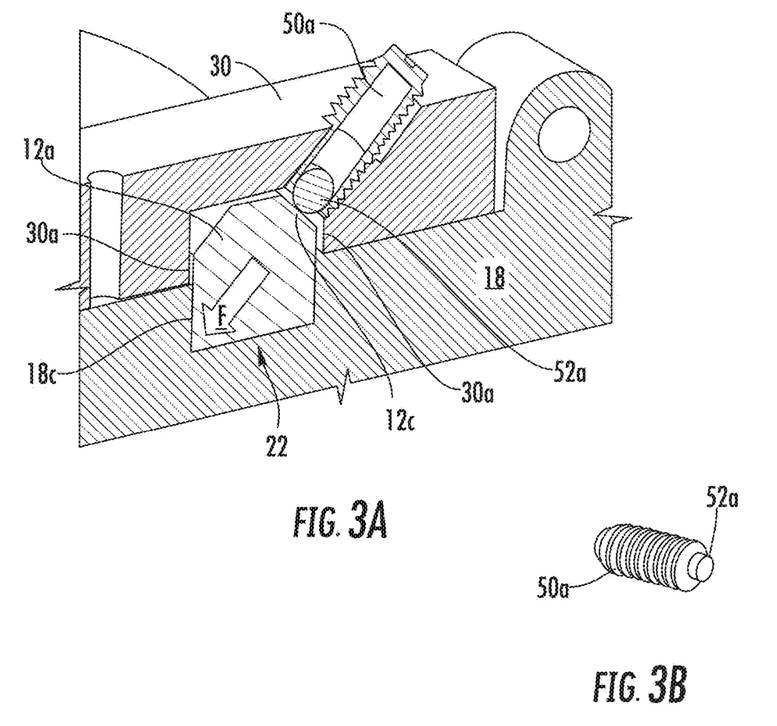
FIG. 3A is cross-sectional view of a portion of a device according to another embodiment of the present disclosure showing the interaction of a biasing member.
FIG. 3B is a perspective view of the biasing member of FIG. 3A.

The movable arm 30 can include at least one biasing member 50a, 50b that applies an individual force toward each receiving space 22 such that each dental blank shaft 12a is held in fixed position relative to the frame 18. FIGS. 3A and 3B are cross-sectional views showing two exemplary biasing member arrangements that may be used with a dental blank holder 10. FIG. 3B is a detail view of the biasing member 50a of FIG. 3A. As shown in FIGS. 3A-3B, the biasing member 50a is a spring plunger that includes a ball 52a. The biasing member 50a can apply a force F toward the receiving space 22, for example, against a corner of recess 18c of the frame 18. In order to apply force F at an angle, the longitudinal direction of biasing member 50a may be disposed through the movable arm 30 at an angle that is aligned with a corner of recess 18c. However, the biasing member 50a may also have a rounded or angled end (e.g., ball 52a) that abuts the dental blank shaft 12a, such that the force F is consistently applied toward the corner of recess 18c—even if the biasing member 50a or dental blank shaft 12a is misaligned relative to the corner of recess 18c. Consequently, the biasing member 50a does not necessarily have to be disposed at an angle that is orthogonal to the surface of angled face 12c of the dental blank shaft 12a to apply a force in the direction F. In one particular example, the biasing member 50a can be made of a stainless steel plunger with a stainless steel ball to provide a maximum force of 5 lbs, with 0.9 mm of deflection.

The force applied by a biasing member may be adjustable. For example, biasing member 50b provides an example of a biasing mechanism whose position, relative to the arm 30, can be adjusted for adjusting the amount of force applied to a dental blank shaft when the arm 30 is in a closed position. For example, the biasing member 50a can be threadedly connected to arm 30 for adjusting the location of biasing member 50a relative to arm 30.

Figure 3C:
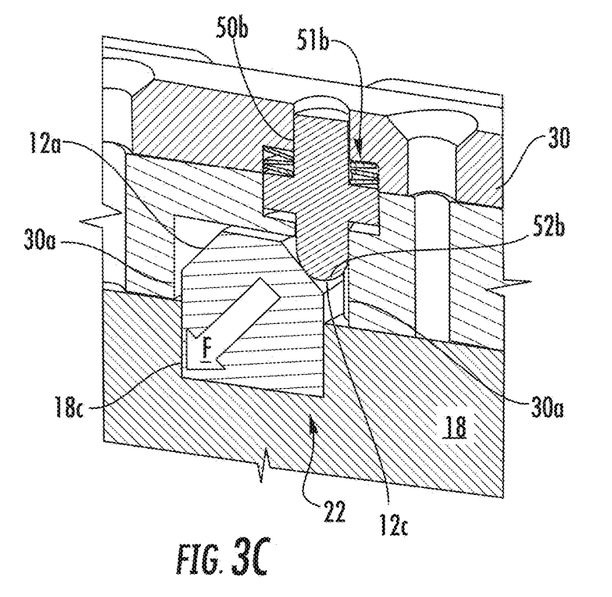
FIG. 3C is a cross-sectional view of a portion of a device according to another embodiment of the present disclosure.

FIG. 3C shows another example of a biasing member 50b that comprises a plurality of Belleville disc springs 51b and a pin 52b. The biasing member 50b can operate in a substantially similar manner as the biasing member 50a by applying a force F toward the corner of recess 18c. The arrangement shown in FIG. 3C also provides an example of the longitudinal direction of biasing member 50b being non-orthogonal relative to the surface of angled face 12c of the dental blank shaft 12a. In one particular example, each Belleville disc spring of springs 51b can provide 18 lbs of load, with 0.006" deflection.

FIGS. 3A and 3C illustrate examples where each dental blank shaft 12a is only contacted in the fixed position by biasing member 50a, 50b and recess 18c—and that movable arm 30 does not otherwise contact the dental blank 12. However, it is contemplated that the dental blank holder 10 according to the present application could be arranged such that the dental blank shaft 12a is also in contact with a movable arm 30 in a closed position.

In operation, the movable arm 30 may be moved from a closed position (FIG. 1A) to an open position (FIG. 1B) by rotating cam 36 about pin 37, for example, by moving an arm attached to the cam 36. Rotating cam 36 can cause arm 30 to pivot about pivot shaft 31, thereby causing biasing members 50a, 50b to move upwardly and away from the frame 18. In the open position, shown in FIG. 1B, one or more dental blanks 12 may be positioned into receiving spaces 22 of blank holder 10. From the open position (FIG. 1B), the cam 36 can be rotated to cause the arm 30 to be moved to a closed position (FIG. 1A). Rotating the cam 36 can cause arm 30 to pivot downwardly against frame 18, such that abutting surfaces 52a, 52b of the biasing members 50 are brought into contact with dental blank shaft(s) 12a positioned in the receiving spaces 22, thereby holding the dental blank shaft(s) 12a for a milling operation to be performed. In a closed position of the dental blank holder 10, about 500N-800N of force can be applied to the dental blank shafts 12a.

Figure 4A:
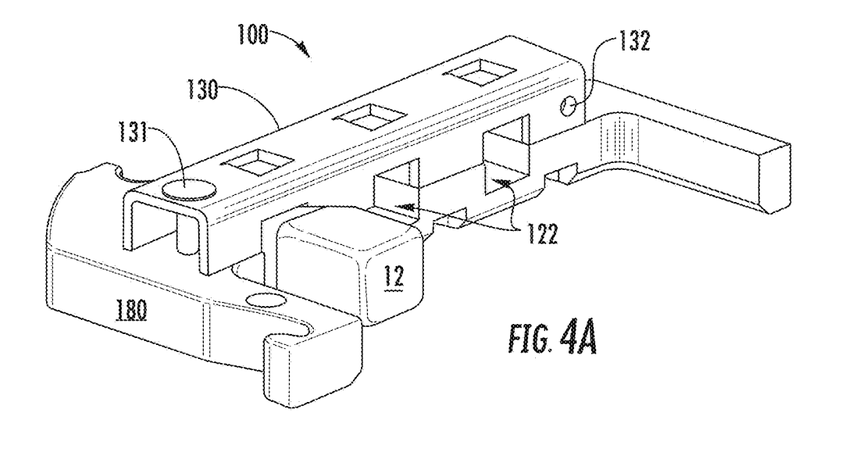
FIG. 4A is a detail view of a portion of a device according to another embodiment of the present disclosure.
Figure 4B:
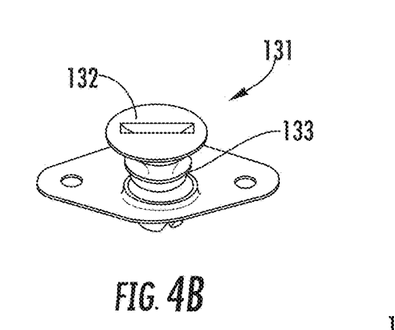
FIG. 4B is a detail view of an exemplary fastener.
Figure 4C:
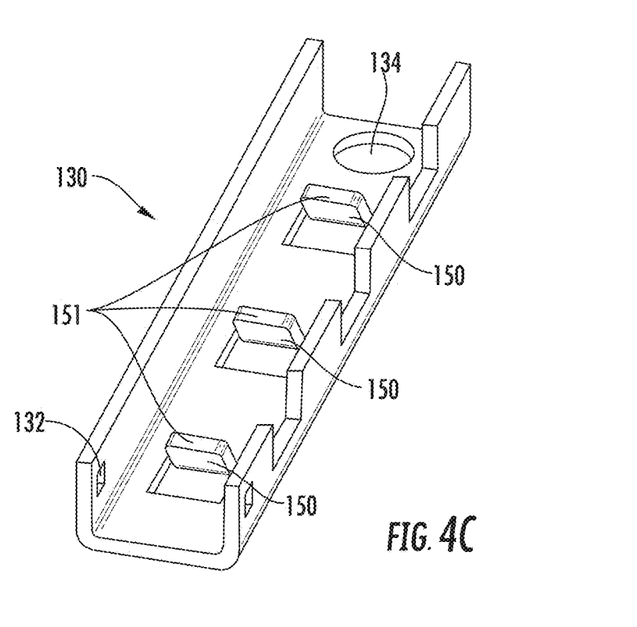
FIG. 4C is perspective view of the arm of the device of FIG. 4A.

FIGS. 4A-4C depict another embodiment of a dental blank holder 100 according to the present disclosure. FIG. 4A is a detail view of one half of the dental blank holder 100 for illustrative purposes only. It should be realized that a full frame 180 may be substantially similar to frame 18 of FIGS. 1A-1B. As shown in FIG. 4A, the movable arm 130 can be pivotable about a pivot rod (not shown) that is disposed through aperture 132 of the movable arm 130. At an opposite end of arm 130, a fastener 131 may be provided to fasten the arm 130 relative to frame 180. FIG. 4B is a detail view of an exemplary fastener 131 which is embodied as a quarter-turn Dzus type fastener that includes screw 132 and spring 133.

As shown in FIG. 4C, the dental blank holder 100 has biasing members 150 which are integrally formed with movable arm 130. In this embodiment, the biasing members 150 and arm 130 can be formed from a single piece of material, for example, sheet metal. The biasing members 150 can be tab-shaped, such each biasing member 150 acts as a cantilever spring that is fixed only at one end. It is contemplated that the abutting surface 151 (i.e., the surface that contacts a dental blank shaft 12a) of biasing member 150 may be rounded, angled, or squared. The movable arm 130 also includes aperture 134 for receiving fastener 131. In a closed position of the dental blank holder 100, about 500N-800N of force can be applied to the dental blank shafts 12a.

In operation, the movable arm 130 may be moved from a closed position (FIG. 4A) to an open position (not shown) by unfastening fastener 131. The fastener 131 may be biased via biasing mechanism 133 such that unfastening fastener 131 pivots the arm 130 upwardly relative to the frame 180. Specifically, the arm 130 may pivot about the rod disposed through aperture 132, such that the arm 130 is brought into the open position. In the open position, one or more dental blanks 12 may be positioned into receiving spaces 122 of blank holder 100. From the open position, the fastener 131 can be fastened relative to the frame 180 to cause the arm 130 to be moved to a closed position. Fastening the fastener 131 can cause arm 130 to pivot downwardly against frame 180, such that abutting surfaces 151 of the biasing members 150 are brought into contact with dental blank shaft(s) 12a positioned in the receiving spaces 122, thereby holding the dental blank(s) 12 for a milling operation to be performed.

Figure 5A:
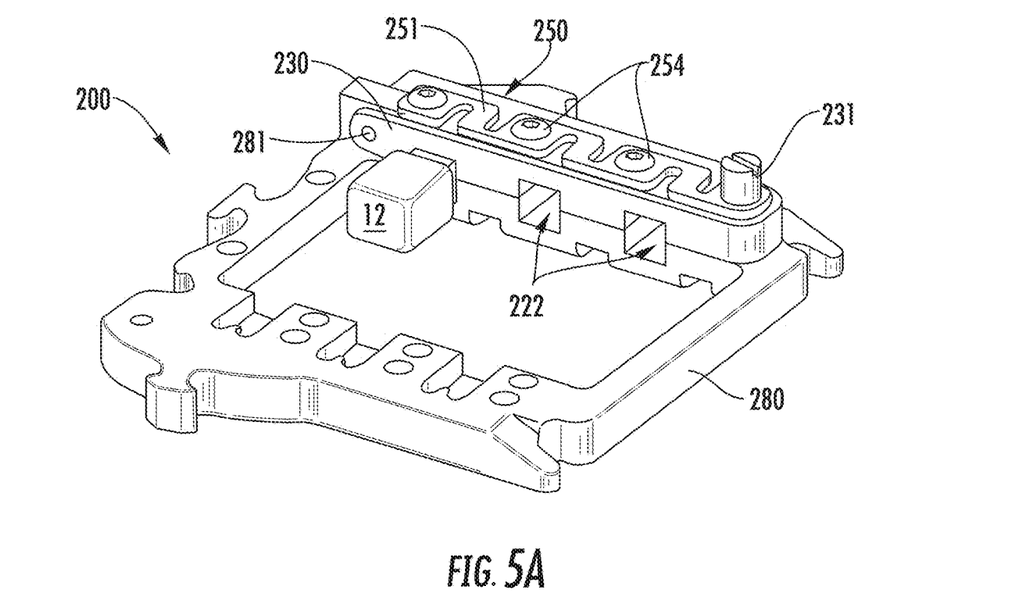
FIG. 5A is a perspective view of device according to another embodiment of the present disclosure.
Figure 5B:
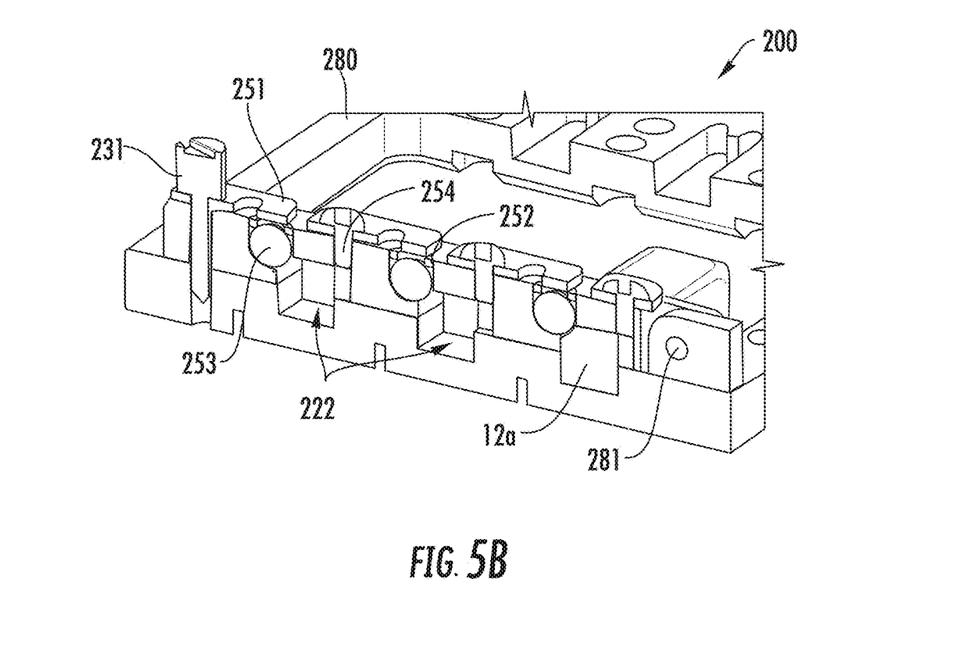
FIG. 5B is a cross-sectional view of the device of FIG. 5A.
Figure 5C:
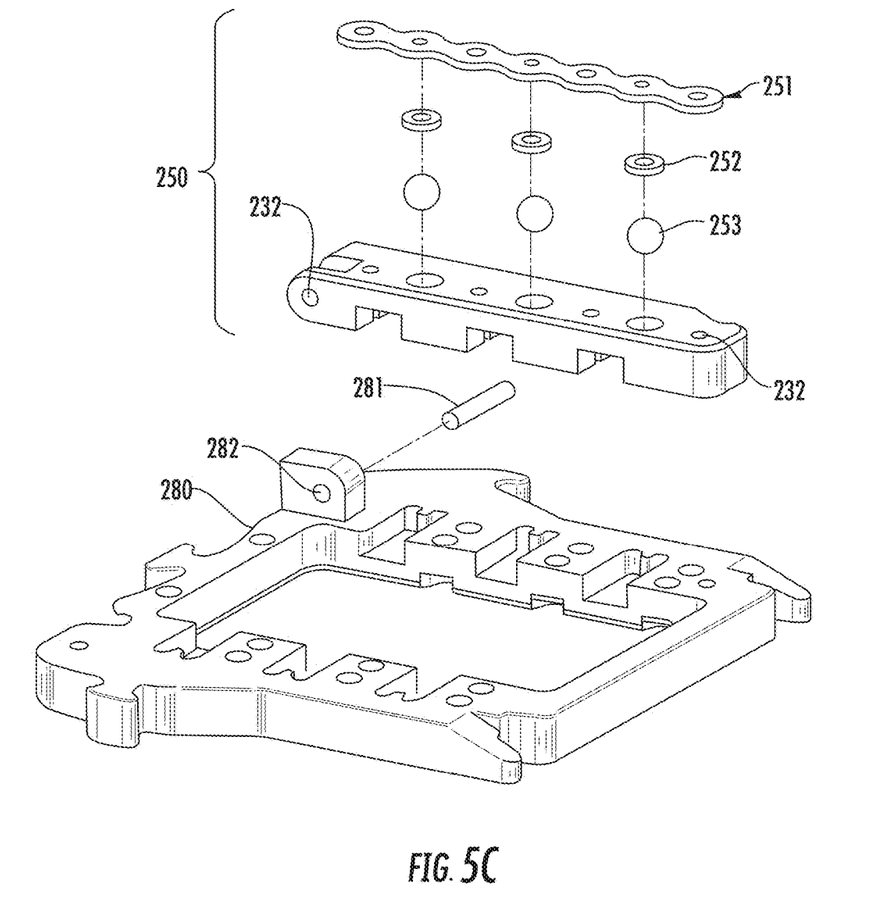
FIG. 5C is an exploded view of the device of FIGS. 5A and 5B.

FIGS. 5A-5C depict another embodiment of a dental blank holder 200 according to the present disclosure. FIG. 5A is a perspective view of the dental blank holder 200 holding an exemplary dental blank 12. FIG. 5B is a sectional view of the dental blank holder 200 of FIG. 5A. FIG. 5C is an exploded view of the dental blank holder 200.

Similar to the dental blank holder 100, the dental blank holder 200 can have a movable arm 230 that is pivotable about a pivot rod 281 disposed through aperture 232 of the movable arm 230 and aperture 282 of frame 280. At an opposite end of arm 230, a fastener 231 may be provided to fasten the arm 230 relative to frame 280. Although a biasing mechanism is not depicted in FIGS. 5A-5C, it is contemplated that the fastener 231 could include a biasing mechanism, similar to the embodiment shown in FIGS. 4A-4C.

The dental blank holder 200 has biasing members 250 that may include a cap 251, bushings 252, and balls 253. The cap 251 can be fastened to the movable arm 230 via fasteners 254 and fastener 231. The balls 253 can be disposed within the movable arm 230. An individual biasing force applied to the dental blank(s) can be provided by the cap 251 and/or balls 253, either or both of which may deform in the presence of a dental blank shaft 12a disposed in receiving spaces 222. In one particular embodiment, the biasing force can be provided by the cap 251, which may be made of a metal, such as a stainless steel. The spring force of the cap 251 can be adjusted by adjusting the type of material, thickness, and/or shape of the cap 251. For example, the serpentine shape of the cap 251 shown in FIGS. 5A-5B, and varying width of cap 251 shown in FIG. 5C, are two exemplary configurations for producing a particular force when the arm 230 is placed in a closed position. In a closed position of the dental blank holder 200, about 500N-800N of force can be applied to the dental blank shafts 12a.

In operation, the movable arm 230 may be moved from a closed position (FIGS. 5A-5B) to an open position (not shown) by unfastening fastener 231. Once unfastened, a user may rotate the arm 230 about pivot rod 281 such that the arm 230 is placed in an open position. In some embodiments, it is contemplated that the arm 230 includes a biasing mechanism for the purposes of urging the arm 230 into an open position. It should also be realized that the biasing mechanism 250 may urge the arm 230 away from a dental blank 12, thereby moving the arm 230 upwardly relative to the frame 280 to some degree. In the open position, one or more dental blanks 12 may be positioned into receiving spaces 222 of blank holder 200. From the open position, the fastener 231 can be fastened relative to the frame 280 to cause the arm 230 to be moved to a closed position. Fastening the fastener 231 can cause arm 230 to pivot downwardly against frame 280, such that balls 253 are brought into contact with dental blank shaft(s) 12a positioned in the receiving spaces 222, thereby holding the dental blank(s) 12 for a milling operation to be performed.

Figure 5D:
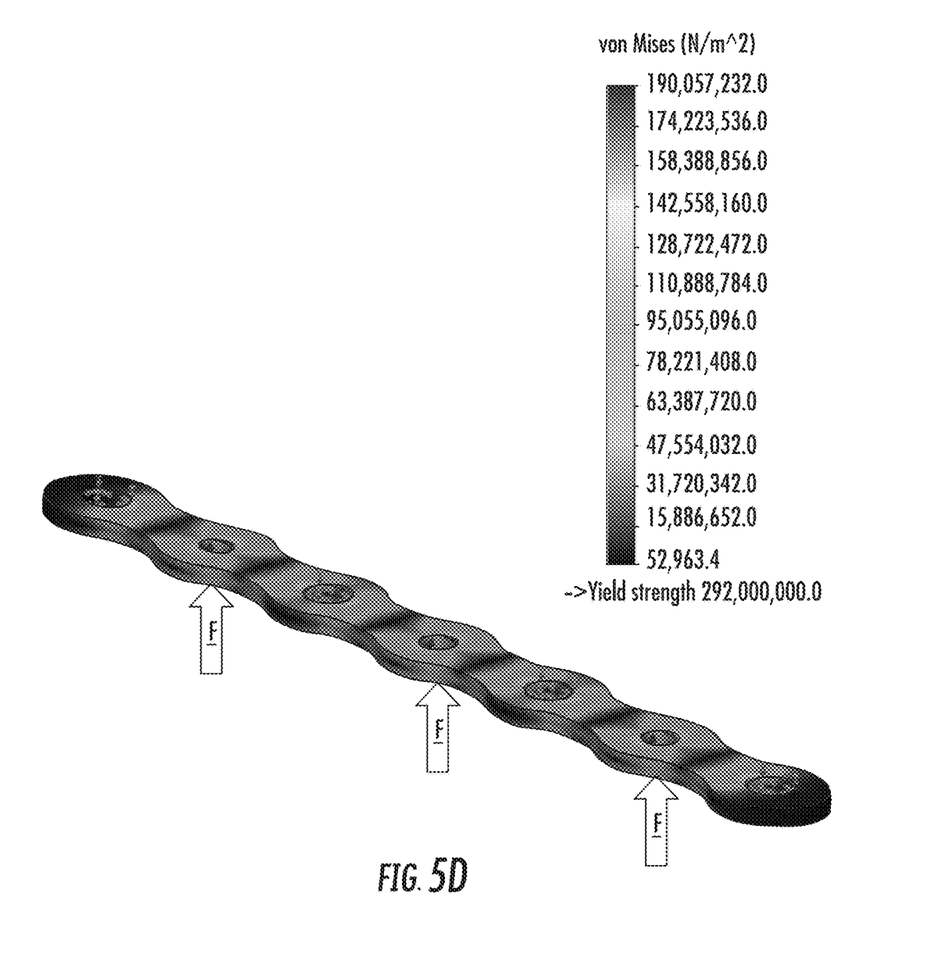
FIG. 5D is a finite element analysis of the cap of FIGS. 5A-5C undergoing a hypothetical force F.

FIG. 5D is a finite element analysis (FEA) of the cap 251 undergoing a hypothetical force F caused by receiving the dental blanks 12 in the dental blank holder 200. The FEA shows the distribution of forces across the cap 251, with the highest amount of forces being applied to the location adjacent balls 253.

Figure 6A:
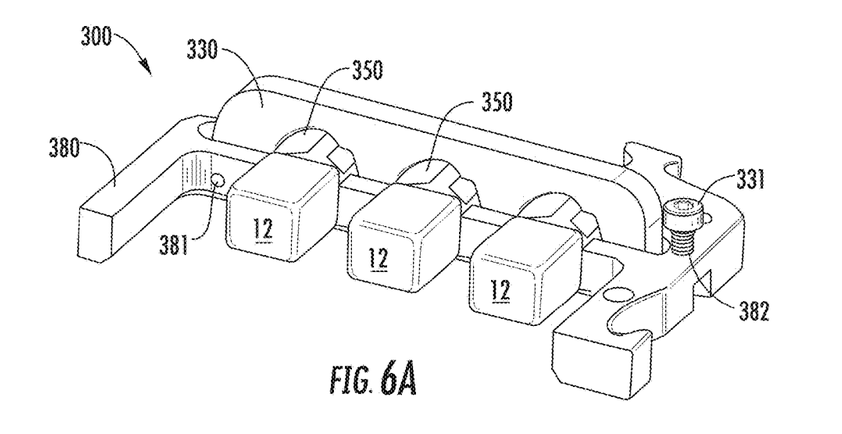
FIG. 6A is a perspective view of a device according to another embodiment of the present disclosure.
Figure 6B:
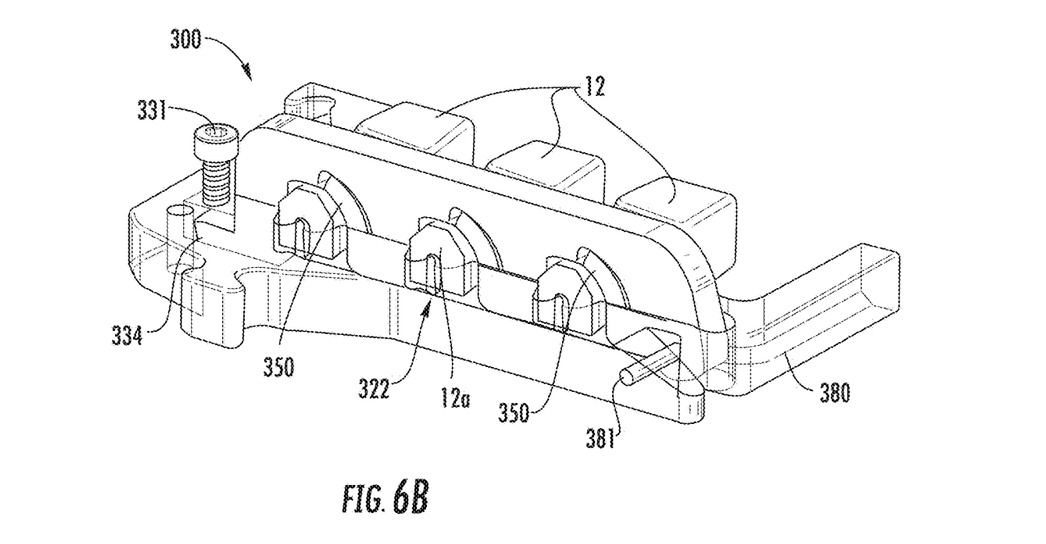
FIG. 6B is another view of the device of FIG. 6A.
Figure 6C:
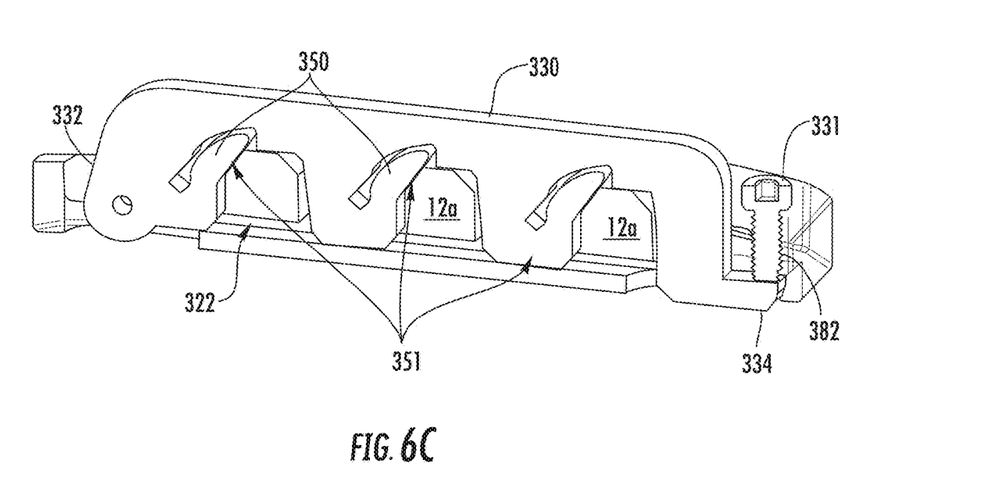
FIG. 6C is a cross-sectional view of a portion of the device in FIG. 6A-6B.

FIGS. 6A-6C depict another embodiment of a dental blank holder 300 according to the present disclosure. FIG. 6A is a detail view of one half of the dental blank holder 300 for illustrative purposes only. It should be realized that the dental blank holder 300 can include a full frame 380 that is substantially similar to frame 18 of FIGS. 1A-1B. FIG. 6B depicts the dental blank holder 300 from an opposite side from FIG. 6A, with the frame 380 being translucent for illustrative purposes. FIG. 6C is a cross-sectional view of the dental blank holder 300, which shows portions of the frame 380 as being translucent for illustrative purposes.

Similar to the dental blank holders 100, 200, the dental blank holder 300 can have a movable arm 330 that is pivotable about a pivot rod 381 disposed through aperture 332 of the movable arm 330 and aperture 382 of frame 380. At an opposite end of arm 330, a fastener 331 may be provided to fasten the arm 330 relative to frame 380. Although a biasing mechanism is not depicted in FIGS. 6A-6C, it is contemplated that the fastener 331 could include a biasing mechanism, similar to the embodiment shown in FIGS. 4A-4C.

The dental blank holder 300 has biasing members 350 that are integrally formed with movable arm 330. In this embodiment, the biasing members 350 and arm 330 can be formed from a single piece of material, for example, a machined piece of metal. The biasing members 350 can be finger-shaped, such that the biasing members 350 act as cantilever springs that are fixed only at one end. Each of the biasing members 350 can have a contact surfaces 351 that are disposed at an angle that is substantially parallel to the angled surface 12c of the dental blank shafts 12a. Fastener 331 engages with aperture 382 of frame 380. The movable arm 330 also includes lip 334 for engaging with fastener 331 to secure arm 330 in the closed position.

In operation, the movable arm 330 may be moved from a closed position (FIGS. 6A-6B) to an open position (not shown) by unfastening fastener 331. Once unfastened, a user may rotate the arm 330 about pivot rod 381 such that the arm 330 is placed in an open position. In some embodiments, it is contemplated that the arm 330 includes a biasing mechanism for the purposes of urging the arm 330 into an open position. It should also be realized that the biasing mechanism 350 may urge the arm 330 away from a dental blank shafts 12a, thereby moving the arm 330 upwardly relative to the frame 380 to some degree. In the open position, one or more dental blanks 12 may be positioned into receiving spaces 322 of blank holder 300. Specifically, the arm 330 may pivot about the pivot rod 381, such that the arm 330 is brought into the open position. In the open position, one or more dental blanks 12 may be positioned into receiving spaces 322 of blank holder 300. From the open position, the fastener 331 can be fastened relative to the frame 380 to cause the arm 330 to be moved to a closed position. Fastening the fastener 331 can cause arm 330 to pivot downwardly against frame 380, such that abutting surfaces 351 of the biasing members 350 are brought into contact with dental blank shaft(s) 12a positioned in the receiving spaces 322, thereby holding the dental blank(s) 12 for a milling operation to be performed.

Figure 6D:
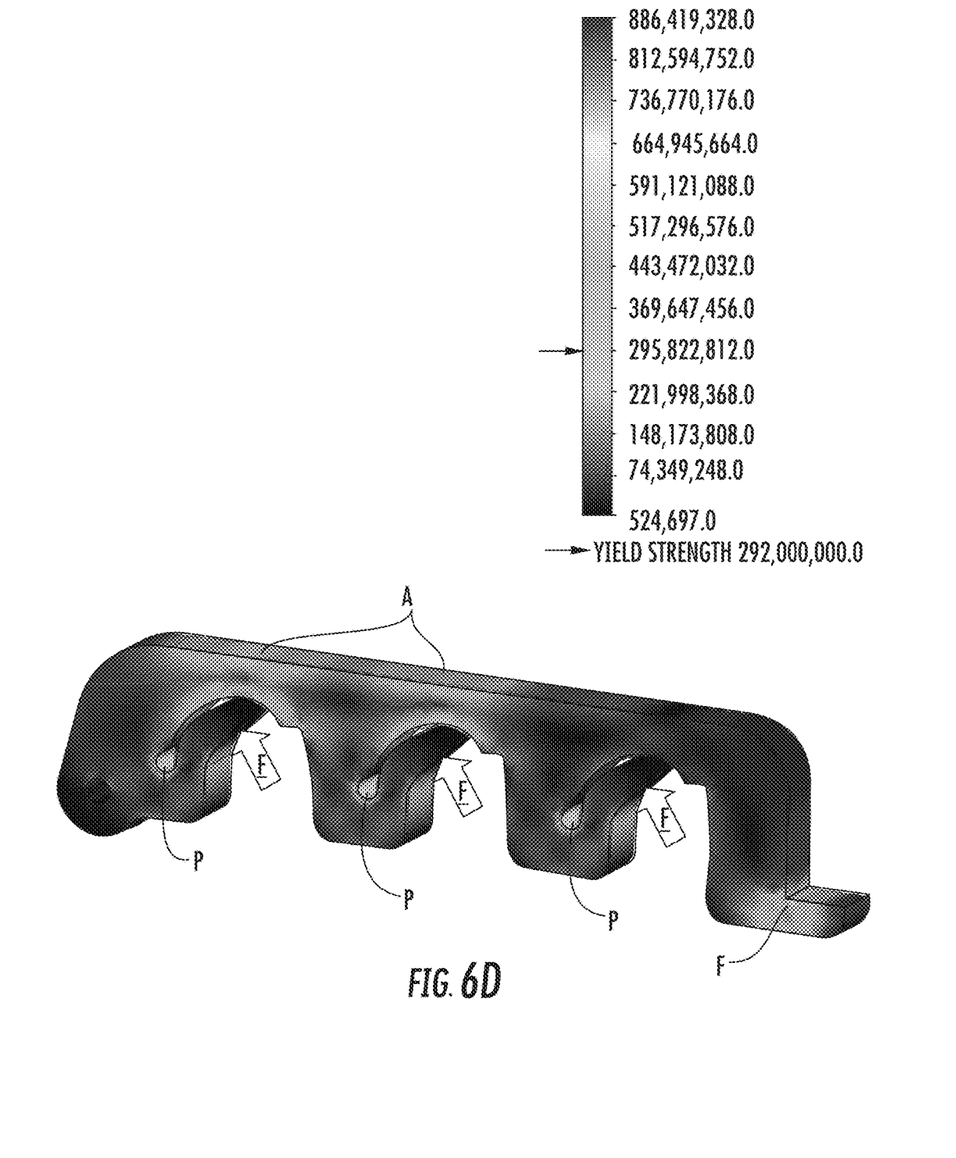
FIG. 6D is a finite element analysis of the arm of the device of FIGS. 6A-6C.
Figure 7A:
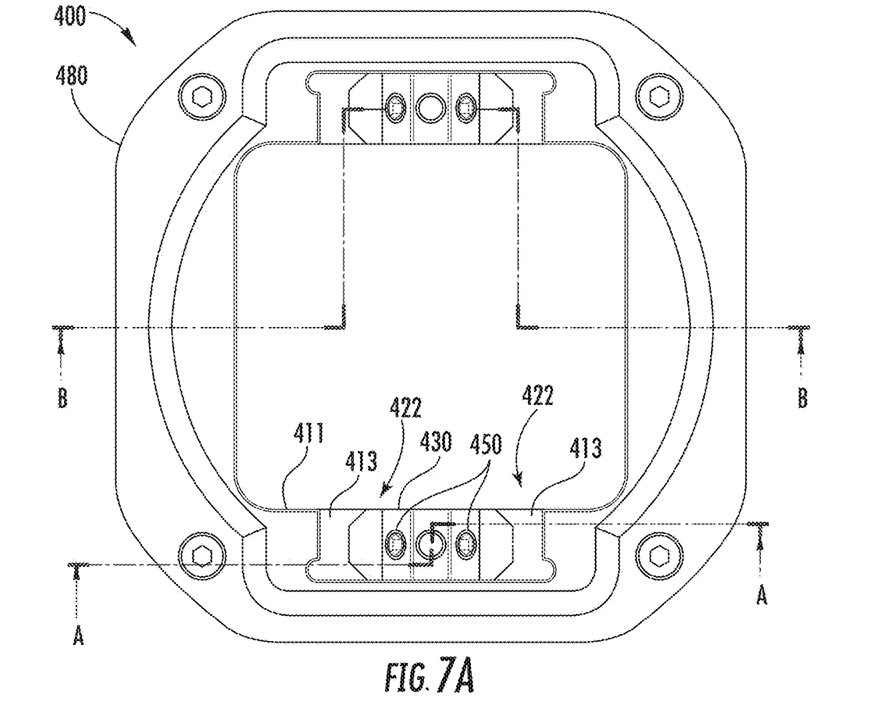
FIG. 7A is a top view of a device according to another embodiment of the present disclosure.
Figure 7B:
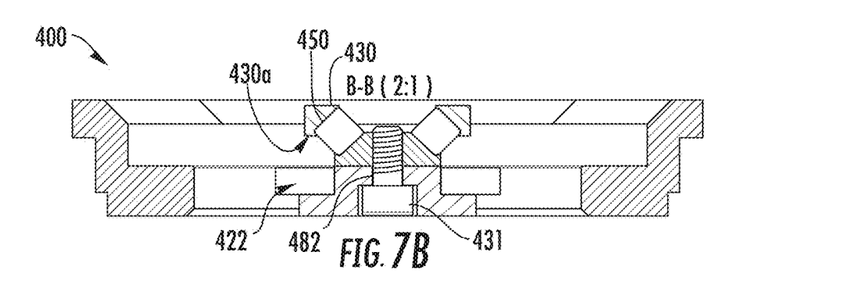
FIG. 7B is a cross-sectional view of the device of FIG. 7A taken along A-A.
Figure 7C:
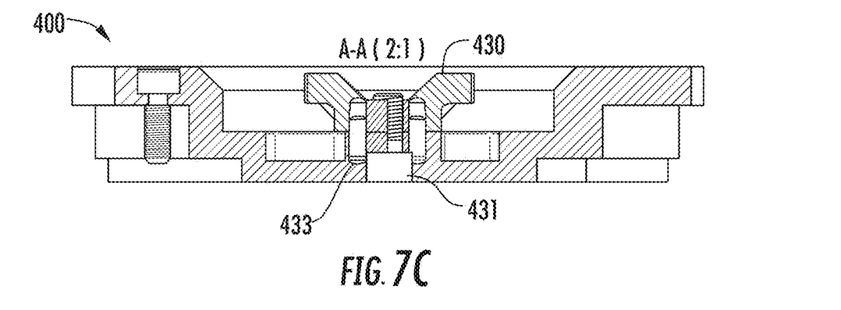
FIG. 7C is a cross-section view of the device of FIG. 7A taken along B-B.
Figure 7D:
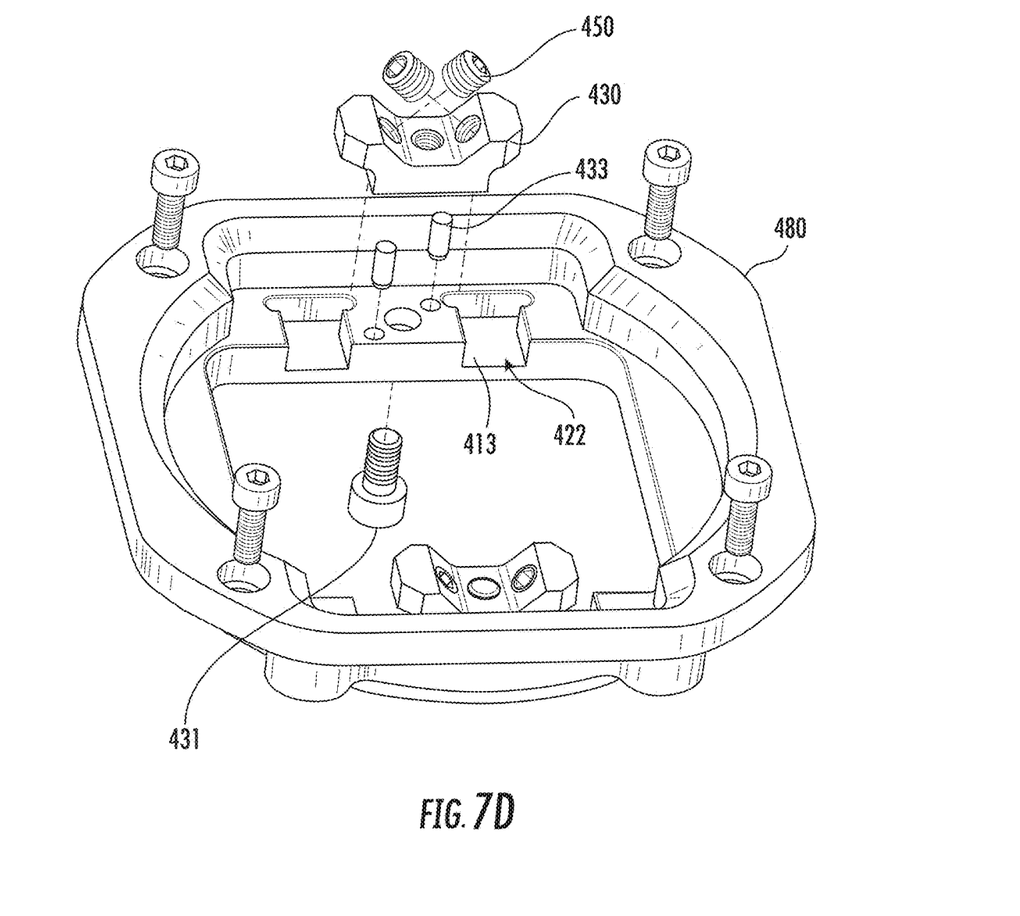
FIG. 7D is a perspective view of the device of FIG. 7A.

FIG. 6D is a finite element analysis (FEA) of the arm 330 and biasing mechanisms 350 undergoing a hypothetical force F caused by receiving the dental blank shafts 12a in the dental blank holder 300. The FEA shows the distribution of forces across the arm 330, with the highest amount of forces being located at the pivot area P of biasing mechanisms 350, an area of the arm that is adjacent the receiving area 322 (area A), and an area of the arm 330 that is adjacent the fastener 331 (area F).

In another embodiment depicted in FIGS. 7A-7D, a holder 400 comprises a frame 480 configured to cooperate with a dental mill. An inner periphery 411 of the frame 480 includes a plurality of receiving walls 413. The receiving walls 413 forming receiving spaces 422, each receiving space 422 configured to receive a dental blank. A moveable arm 430 is configured to form a plurality of locking walls 430a (in the depicted embodiment, two locking walls 430a). Each locking wall 430a is configured to enclose a corresponding receiving space 422. The moveable arm 430 includes at least one biasing member 450 for applying an individual force toward each receiving space 422. In this way, each of the dental blanks is held in a receiving space 422 for milling.

Moveable arm 430 is secured to the frame 480 by way of fastener 431 through aperture 482 of frame 480. The holder 400 may further comprise one or more pins 433 for aligning moveable arm 430. Pins 433 may further prevent rotation of moveable arm 430, for example, while the fastener 431 is being tightened.

Although the present disclosure has been described with respect to one or more particular embodiments, it will be understood that other embodiments of the present disclosure may be made without departing from the spirit and scope of the present disclosure. Hence, the present disclosure is deemed limited only by the appended claims and the reasonable interpretation thereof.

What is claimed is:

1. A dental blank holder for the manufacture of dental articles, comprising:
   a frame configured to cooperate with a dental mill, the frame comprising an inner periphery and an outer periphery, the inner periphery including a plurality of receiving walls forming receiving spaces, each receiving space configured to receive a dental blank;
   a movable arm configured to form a plurality of locking walls, each locking wall configured to enclose a corresponding receiving space, the movable arm including at least one biasing member configured to apply an individual force toward each receiving space such that each of the dental blanks is held in the receiving spaces for a milling process;
   wherein the movable arm is pivotable between an unlocked position where the dental blanks can be removed from the receiving spaces, and a locked position where the dental blanks are locked for a milling operation by the dental mill.

2. The dental blank holder of claim 1, wherein the locking walls are configured to be spaced apart from the dental blanks received by the blank holder.

3. The dental blank holder of claim 1, wherein the individual force applied by the biasing member is in a direction that is non-orthogonal to a surface of the locking wall of the plurality of receiving spaces and non-orthogonal to a surface of each of the receiving walls of each of the plurality of receiving spaces.

4. The dental blank holder of claim 1, wherein the individual force is configured to be applied to a portion of each of the respective dental blanks that is not received by the plurality of receiving walls or the locking wall.

5. The dental blank holder of claim 1, wherein each of the at least one biasing member includes a respective rounded surface that is configured to be in direct contact with a wall of the respective dental blanks.

6. The dental blank holder of claim 1, wherein the movable arm is placed in the locked position via engagement of a single locking mechanism.

7. The dental blank holder of claim 1, further comprising a cam mechanism coupled to the movable arm, the cam mechanism being rotatable between a first position and a second position;
   wherein in the first position of the cam, the movable arm is placed in the locked position, and in the second position of the cam, the movable arm is placed in the unlocked position.

8. The dental holder of claim 1, wherein the at least one biasing member includes a spring plunger and ball, the ball configured to cooperate with a surface of the dental blank.

9. The dental blank holder of claim 1, wherein the at least one biasing member includes a plurality of disc springs and a pin, the pin configured to cooperate with a surface of the dental blank.

10. The dental blank holder of claim 1, wherein the at least one biasing member is integrally formed with the movable arm.

11. The dental blank holder of claim 10, wherein the at least one biasing member is a cantilever spring.

12. The dental blank holder of claim 1, wherein the movable arm is hingedly mounted to the frame.

13. The dental blank holder of claim 12, further comprising a rotatable fastener coupled to the movable arm, the rotatable fastener being rotatable between a first position and a second position;

wherein in the first position of the rotatable fastener, the movable arm is placed in the locked position, and in the second position of the rotatable fastener, the movable arm is placed in the unlocked position.

14. The dental blank holder of claim 1, wherein the at least one biasing member includes a ball and an elastic ball cap, the ball cap being positioned at an outer surface of the movable arm.

15. The dental blank holder of claim 14, wherein the ball cap extends across the plurality of receiving spaces.

16. The dental blank holder of claim 1, wherein the movable arm forms a plurality of locking walls about each of the receiving spaces.

17. The dental blank holder of claim 16, wherein the movable arm forms the at least one biasing member.

18. A dental blank holder system for the manufacture of dental articles, comprising:

a dental mill;

a plurality of dental blanks;

a frame configured to cooperate with the dental mill, the frame comprising an inner periphery and an outer periphery, the inner periphery including a plurality of receiving walls forming receiving spaces, each receiving space configured to receive a respective dental blank of the plurality of dental blanks;

a movable arm configured to form a plurality of locking walls, each locking wall configured to enclose a corresponding receiving space, the movable arm including at least one biasing member configured to apply an individual force toward each receiving space such that each of the dental blanks is held in the receiving spaces for a milling process; and wherein the movable arm is pivotable between an unlocked position where the dental blanks can be removed from the receiving spaces, and a locked position where the dental blanks are locked for a milling operation by the dental mill.

19. The dental blank holder system of claim 18, wherein the dental blanks have a hexagonal cross-section.

* * * * *